(12) United States Patent
Hahn et al.

(10) Patent No.: US 6,699,711 B1
(45) Date of Patent: Mar. 2, 2004

(54) DEVICE AND METHOD FOR SELECTIVE EXPOSURE OF A BIOLOGICAL SAMPLE TO SOUND WAVES

(75) Inventors: Thomas Hahn, St. Ingbert (DE); Bernhard Kleffner, Kleinblittersdorf (DE); Hans Ruf, Neunkirchen (DE)

(73) Assignee: Fraunhofer-Gesellschaft zur Forderung der angewandten Forschung e.V., Munich (DE)

( * ) Notice: Subject to any disclaimer, the term of this patent is extended or adjusted under 35 U.S.C. 154(b) by 0 days.

(21) Appl. No.: 09/674,813

(22) PCT Filed: Apr. 23, 1999

(86) PCT No.: PCT/DE99/01233
§ 371 (c)(1),
(2), (4) Date: Jan. 4, 2001

(87) PCT Pub. No.: WO99/58637
PCT Pub. Date: Nov. 18, 1999

(30) Foreign Application Priority Data

May 7, 1998 (DE) .......................... 198 20 466

(51) Int. Cl.[7] .......................... C12M 1/02; C12M 1/33; C12N 1/06
(52) U.S. Cl. .......................... 435/283.1; 435/303.3; 435/305.2; 435/306.1; 435/259; 241/2; 366/114; 366/127
(58) Field of Search ................. 435/259, 283.1, 435/286.7, 303.3, 305.1, 305.2, 306.1; 241/2; 366/127, 114

(56) References Cited

U.S. PATENT DOCUMENTS

| | | | | |
|---|---|---|---|---|
| 3,979,711 A | * | 9/1976 | Maginness et al. | 367/87 |
| 4,571,087 A | * | 2/1986 | Ranney | 366/108 |
| 5,736,100 A | * | 4/1998 | Miyake et al. | 422/64 |
| 6,086,821 A | * | 7/2000 | Lee | 422/20 |

FOREIGN PATENT DOCUMENTS

| | | | | |
|---|---|---|---|---|
| DE | 4241154 C1 | * | 3/1994 | B01D/51/08 |
| EP | 271448 A2 | * | 6/1988 | B01F/11/00 |
| EP | 337690 A1 | * | 10/1989 | B01L/3/14 |
| EP | 353365 A2 | * | 2/1990 | C12M/3/00 |
| GB | 938163 A | * | 10/1963 | |

* cited by examiner

Primary Examiner—William H. Beisner
(74) Attorney, Agent, or Firm—Mintz, Levin, Cohn, Ferris, Glovsky and Popeo, P.C.

(57) ABSTRACT

A device and method are disclosed for selective exposure of a biological sample, preferably biological cell material, to sound waves. The device is provided with a receptacle for the sample, in which the biological sample is in a suspended form, and having an electroacoustic transducer device, which generates sound waves and which is disposed outside the receptacle of the sample in such a manner that sound-wave coupling into said sample occurs through the wall of said receptacle.

54 Claims, 3 Drawing Sheets

DEVICE AND METHOD FOR SELECTIVE EXPOSURE OF A BIOLOGICAL SAMPLE TO SOUND WAVES

FIELD OF THE INVENTION

Figure 2:
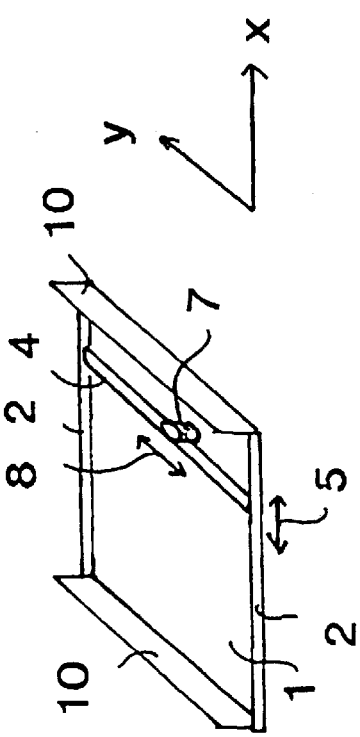
Figure 1:
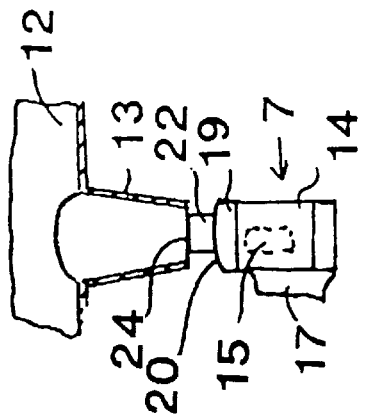

The present invention relates to a device for selective exposure of a biological sample, preferably biological cell material or tissue samples, to sound waves, comprising a receptacle for the sample in which the biological sample is found in a suspended form and an electroacoustic transducer device which generates the sound waves and is disposed outside the receptacle for the sample in such a manner that sound-wave coupling occurs through the wall of the receptacle of the sample into the sample.

BACKGROUND OF THE INVENTION

A multiplicity of applications of sound waves in the form of ultrasonic power for influencing the properties of a material or the structure of a material are known. For example, ultrasonic lithotriptors use ultrasound to crush kidney stones and gallstones. Furthermore, ultrasound is utilized for cleaning wounds and for phacoemulsification. In non-medical fields, ultrasound is employed, for example, for cleaning, boring, milling and welding.

Exposure of biological samples to ultrasound can trigger certain biological effects, for instance transportation of cells into cell reactors without impairing cell vitality, indeed destroying the cells, as is the case with the aforementioned lithotriptors. Due to the disintegrating effect on biological structures, ultrasonic emulsificators attained considerable significance in breaking down samples.

Such ultrasonic emulisifactors, so-called sonotrodes often have rapid transformers disposed on electroacoustic transducers such as for example Langevin's or composite oscillators. The electroacoustic transducers frequently are provided with piezoceramic as the active material and oscillate with an amplitude of, for example, 0.5 $\mu$m. With the aid of transformers, the initially very small amplitude is multiplied, for example, to over 500 $\mu$m.

These ultrasonic emulsificators have proven themselves in practice and are often used. The effect of sound transmitted from the sonotrode to the biological sample depends on the sound pressure amplitude, which may vary strongly spatially due to the interference of sound waves reflected at the receptacle of the sample. As the temperature and location of the tip of the sonotrode in the sample strongly influence interferences and the sample usually warms up during treatment, it is difficult to dose ultrasound precisely for selective excitation of biological effects.

Furthermore, there is the danger of cross contamination from dipping the sonotrode in the sample if the sonotrode is not cleaned with the necessary care when changing samples.

The traditional design of the device does not prevent the foam or aerosol formation, which reduces the reproducibility of sound-wave exposure.

As, for electroacoustic reasons, sonotrodes cannot be designed as small as possible, there are limits to treating miniaturized samples such as are, e.g., used in breaking down samples for genetic analyses.

DE 32 09 841 C2 describes an arrangement for embedding at least one tissue sample in paraffin. The device provides a receptacle into which various coupling liquids can be introduced into which a certain sample of tissue to be treated is placed. To accelerate the willingness of the sample tissue to react with the respective liquids inside the receptacle, the device provides on the bottom of the receptacle an ultrasound generator 61, which couples ultrasonic waves with a frequency of 35 KHz into the interior of the work receptacle. However, with the selected frequencies, ultrasonic energy cannot be concentrated on very small sample volumes. Moreover, the device known from the art provides for disposing the ultrasound generating unit both inside and outside the sample receptacle. Therefore, it can be assumed that, in this case, there is no cross contamination problem.

The desire for concentrated introduction of ultrasonic waves in, for example, biological material is borne by the attempt to generate the desired process respectively reactions inside the cell material. A typical example of such a process is breaking down cells in order to examine the interior of the cells in subsequent detection processes.

As mentioned in the preceding, for breaking down the cell, ultrasonic waves which generate shear forces due to the biological cells in a suspension are employed, among other things, thereby breaking open the cell walls. In order to improve the effect of breaking open the cell, measures are undertaken to enhance the shear forces inside the suspension. For example, additional macroscopic particles, preferably in the form of small glass beads, are introduced into the suspension in order to enhance the action of the shear forces on the individual cells responsible for breaking them up.

In addition to the desire to enhance the shear forces acting on the cells, there is the need to miniaturize such types of devices, which seems to be in contradiction with the desire to enhance the shear forces.

SUMMARY OF THE INVENTION

The object of the present invention is to provide a device for exposing biological samples, preferably biological cell material, to sound waves, permitting precise intensity dosage of sound waves for selective excitation of biological effects. Furthermore, measures should be undertaken to increase the energy input in relation to the limited sample volume. In addition to the aforementioned requirements, it should be possible to miniaturize the size of the device in order to be able to conduct a large number of sample tests.

This object is solved with a device having the features of claim 1. Advantageous embodiments are described in the subclaims.

The invented device for selective exposure of a biological sample, preferably biological cell material, to sound waves, having a sample receptacle, in which the sample is in suspended form, and an electroacoustic transducer device, which is disposed outside the receptacle of the sample and which generates sound waves in such a manner that coupling the sound waves into the sample occurs through the wall of the sample receptacle, is further improved in such a manner that the electroacoustic transducer device generates sound waves having a frequency of at least 100 kHz, preferably of 500 kHz to 5 MHz, and that means for focusing the sound waves are provided which concentrate the sound waves approximately to 50 $\mu$l on a sample volume inside the sample receptacle.

In the invented ultrasonic device, the electroacoustic transducer device interacts with the receptacle of the sample in such a manner that the ultrasonic coupling into the sampleoccurs through the wall of the receptacle of the sample and the electroacoustic transducer device is disposed outside the receptacle of the sample. As the sound, unlike in conventional ultrasonic emulsificators, is not radiated from the inside to the outside but from the outside to the inside, sound intensity distribution is limited to the sample so that in conjunction with a high mean frequency, lying in ranges of more than 100 kHz, the influence of the interference of the sound waves reflected at the wall of the receptacle for the sample can be controlled. This measure permits exact dosage of sonic intensity and precise excitation of certain biological effects in the sample volume down to 50 $\mu$l and below. Typical sample volumes in which selective biological effects can be generated are approximately 100 $\mu$l.

In an advantageous embodiment, sound coupling occurs through the floor of the sample receptacle in such a manner that the major part of the sound waves enters focused from below upward through the sample and is reflected at the top interface with reduced reflection at the wall of the sample receptacle. This is a very effective arrangement for controlling disturbing interferences.

For optimization of the intensity coupling, preferably a plane-parallel acoustic $\lambda/4$ wave transformer is provided in the wall of the receptacle of the sample.

By inserting an acoustic lens in the wall of the receptacle of the sample, sound intensity distribution can be concentrated on a prescribed area of the volume in the sample receptacle.

The acoustic lens is preferably designed as a spherical acoustic lens and is insertable in the bottom of the sample receptacle or forms it completely.

Preferably sound-wave coupling occurs in the sample receptacle by means of structure-borne sound by providing a coupling element containing a soft polymer element or a liquid between the electroacoustic transducer device and the receptacle of the sample and being in immediate contact with the two or by providing a liquid coupling.

The invented selection of the used ultrasonic frequencies of at least 100 kHz, preferably 500 kHz to 5 MHz, permits focusing such high-frequency sound waves on the smallest areas, with their spatial sound intensity distribution being precisely influenceable. Thus, with such high-frequency sound waves, the area of maximum sound pressure can be focused on the center of the sample volume, thereby obviating spraying on the surface (aerosol formation) and therefore any cross contamination of adjacent samples.

Moreover, acoustic coupling at the wall of the receptacle of the sample by means of structure-borne sound is essentially free of losses so that small transducer devices suffice to generate sound. As they are disposed outside the sample receptacle, they can also be of very simple design in order to be able to provide the sound frequency required for the ultrasonic treatment of the biological samples. The invented ultransonic device can, therefore, be miniaturized and be employed with micro-titer plate systems.

Sound-wave coupling in the sample through the wall of the receptacle of the sample is not subject to changing parameters, which makes them exactly reproducible. Exact reproducibility of sound-wave coupling is a prerequisite for exact dosage and automated sample processing, in which the receptacle of the sample is automatically replaced respectively in which the biological sample in a sample receptacle is automatically exchanged.

BRIEF DESCRIPTION OF THE DRAWINGS

The present invention is made more apparent by way of example in the following without the intention of limiting the scope or spirit of the inventive idea with reference to the accompanying drawings depicting in:

FIG. 1 an exploded view of an invented ultrasonic device and a kind of exploded view of a micro-titer plate above the ultrasonic device, FIG. 2 an electroacoustic transducer device employed in the ultrasonic device of FIG. 1 and a section through a sample receptacle for the micro-titer plate of FIG. 1, FIG. 3 an invented ultrasonic device having a piezoelectric composite, an electronic control means and a micro-titer plate provided with a multiplicity of sample receptacles.

FIGS. 4*a* and 4*b* a REM image of a piezoelectric composite and an exploded schematic view of a composite, and FIGS. 5*a* to 5*e* the fabrication steps for fabricating a piezoelectric composite.

DETAILED DESCRIPTION OF THE INVENTION

FIG. 1 shows a first preferred embodiment of a device for selective exposure of a biological sample, preferably biological cell material, to sound waves.

This device is provided with a plane base plate 1, which is provided with rails 2 at two opposite lateral edges respectively. Borne on the rails 2 is a tie-bar 4, which is moveable in the longitudinal direction of rail 2 (double arrow 5) and is driven by an electric engine (not shown) for moving along rails 2.

Disposed in a moveable manner on tie-bar 4 is an electroacoustic transducer device 7 which can be driven to and fro by another electric engine (not shown) along the tie-bar 4 (double arrow 8) in longitudinal direction.

Lateral walls 10 are provided at the lateral edges of base plate 1 running parallel to tie-bar 4 for receiving a micro-titer plate 12. Micro-titer plate 12 is a plastic plate provided with a multiplicity of recesses arranged in a regular grid. These recesses each form a sample receptacle 13 respectively for receiving chemical and biological and, in particular, micro-biological samples. Micro-titer plate 12 is placed on the invented device, being borne by lateral walls 10. The electroacoustic transducer device 7 is moveable in the x and y direction in the plane of the base plate 1 in such a manner that the electromagnetic transducer device 7 can be disposed under all the sample receptacles 13 of micro-titer plate 12. FIG. 2 shows a lateral view of this electroacoustic transducer device 7 having an approximately cylindrical body 14 made of a material that transmits sound well, such as for example a polymer, in which an electroacoustic transducer 15 is embedded. The electroacoustic transducer 15 is preferably made of a piezoelectric, magnetostrictive and/or electrostrictive material that can transduce the electromagnetic waves into sound waves.

Body 14 surrounding the electroacoustic transducer 15 is secured to the tie-bar 4 by a holding means 17.

The entire device can also be filled with liquid, obviating coupling cushions.

An acoustic lens 19 having a spherical surface 20 is disposed on the upward facing front of body 14. With the aid of this acoustic lens 19 the sound waves emitted from the electroacoustic transducer 15 are bundled, yielding thereby a sharply focused ultrasonic beam.

A coupling element 22 for coupling the ultrasonic beam into the sample receptacle 13 is provided in the center of the spherical surface 20 of the acoustic lens 19. The coupling element 22 is made, for example, of a soft loss-free polymer or can be made of a thin-walled plastic receptacle filled with a liquid suited for transmitting sound. A liquid suited for transmitting sound is, for example, water or preferably degassed water.

The tie-bar 4 is preferably provided with a tilting means (not shown) with which the electroacoustic transducer 15 and the coupling element 22 can be raised and pressed against the sample receptacle 13, with the coupling element 22 lying immediately on the floor of the receptacle 24.

The micro-titer plates are preferably made of good sound-transmitting polymer materials, such as polystyrol, polypropylene or polyethylene, and the contact areas of the receptacles 13 to the electroacoustic transducer device 7—in the depicted preferred embodiment they are the floors of the receptacle 24—are preferably designed membrane-like or, in particular, form plane-parallel acoustic λ/4-wave transformers. However, within the scope of the present invention, instead of the acoustic lens 19 being disposed in the electroacoustic transducer device 7, the floor of the receptacle 24 of the sample receptacle 13 can be designed as the acoustic lens having a spherical surface.

Essential for the present invention is that the sound-wave coupling into the sample in the sample receptacle 13 occurs through the wall of the sample receptacle in such a manner that the sound is coupled by means of structure-borne sound with exactly defined conditions. This coupling by means of structure-borne sound has small losses so that the sound intensity required for treating the sample materials can be provided even with small electroacoustic transducers. By focusing with the acoustic lens 19, the sound waves are concentrated on the sample material, resulting in very effective exploitation of the sound wave energy. Moreover, the invented electroacoustic transducer device 7 does not come directly in contact with the sample material so that it can quickly be moved between the individual sample receptacles 13 of a micro-titer plate 12 without any risk of contamination. As, due to the very effective coupling, the intensities generated by the transducer 15 can be very small, the electroacoustic transducer 15 can be miniaturized. As the transducer does not come in contact with the sample material during coupling and can be moved quickly between the individual sample receptacle 13 without additional cleaning, the invented ultrasonic device is ideally suited for automated ultrasonic treatment of a multiplicity of samples.

High-frequency ultra sound having a frequency of at least more than 100 kHz and, in particular, from 500 kHz to 5 MHz, can be employed as the ultra sound, because high-frequency sound can be focused on very small volumes so that even sample volumes of approximately 50 μl can be exposed to sound separately. The maximum sound pressure can be focused in the center of the sample volume thereby preventing spraying at the surface (aerosol formation) and therewith cross contamination of sample material of adjacent sample receptacles 13.

Figure 3:
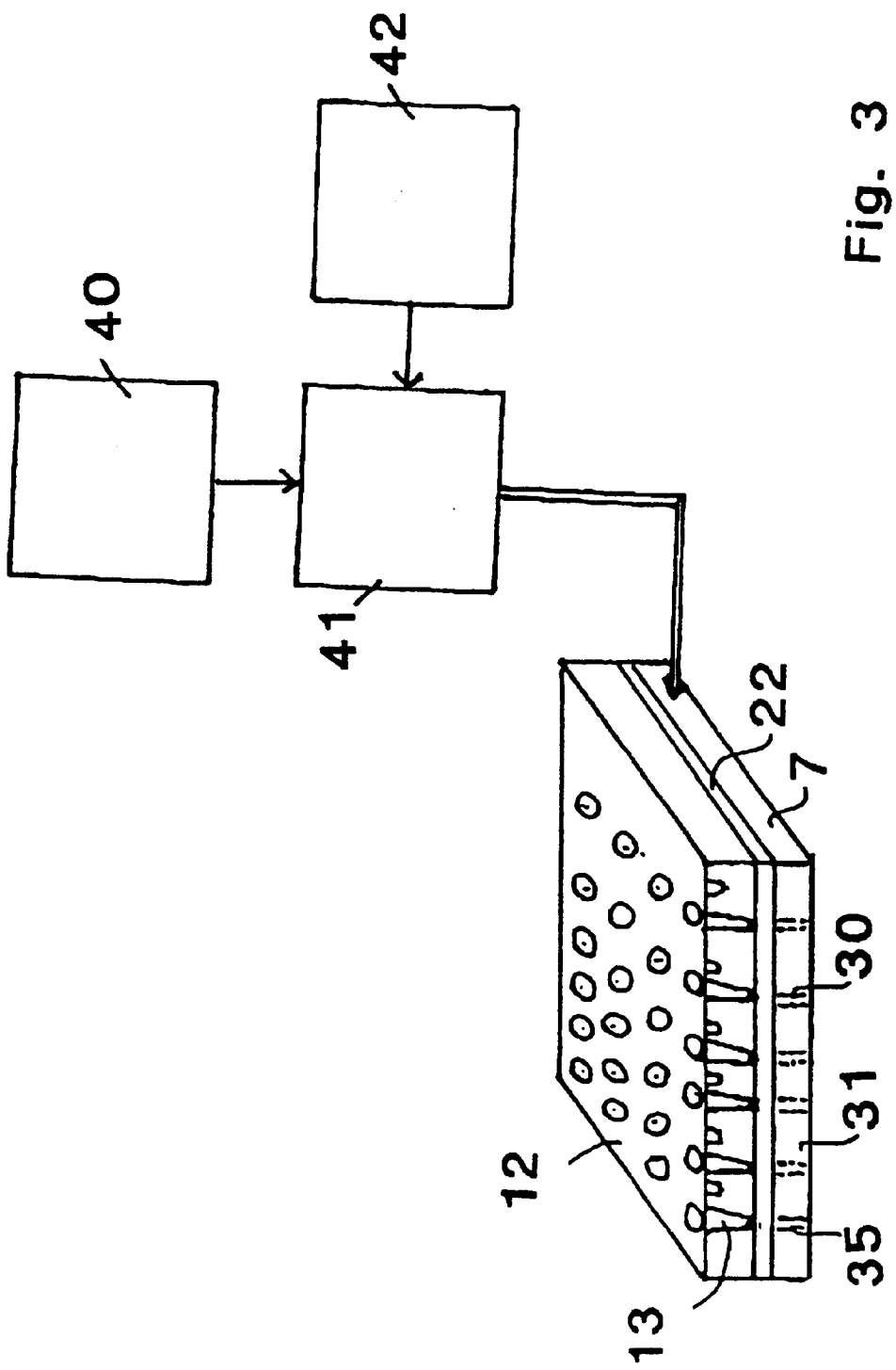
Figures 4A, 4B:
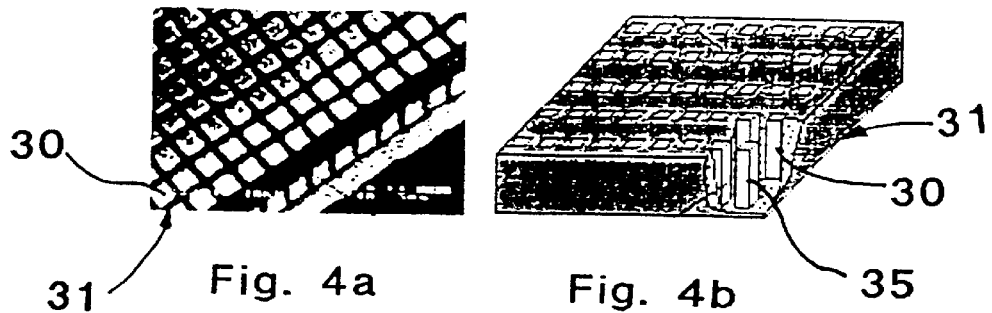
Figure 5:
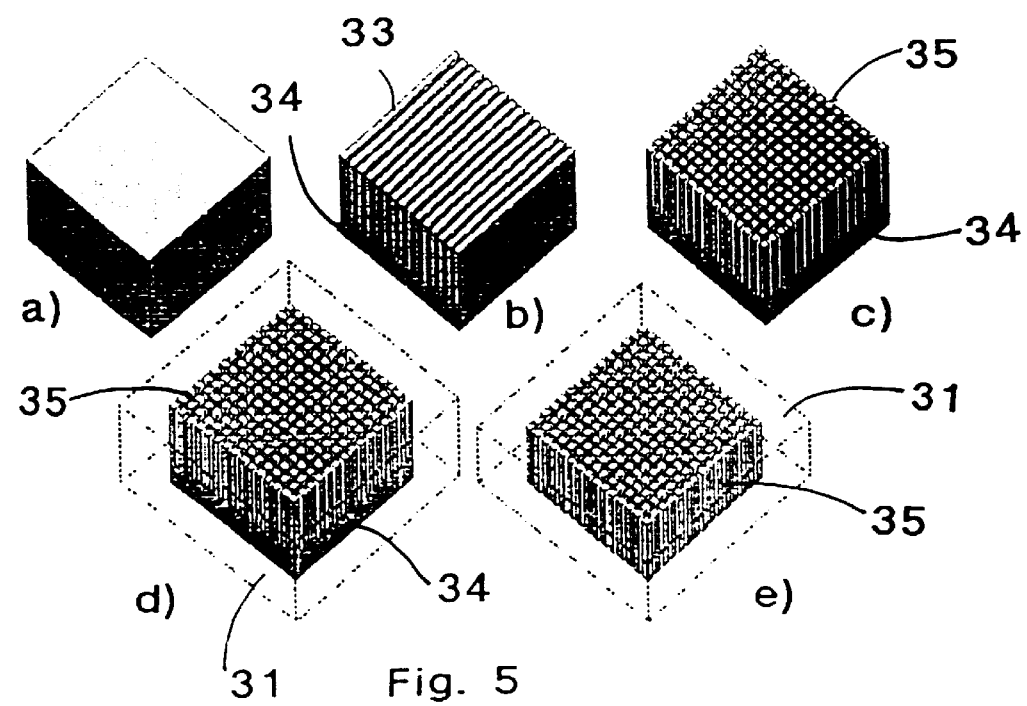

Another preferred embodiment of the present invention for selective exposure of a biological sample to sound waves is schematically shown in FIGS. 3 to 5e. This ultrasonic device is provided with a so-called piezoelectric 1–3 composite as the electroacoustic transducer device 7. In such a piezoelectric 1–3 composite, a multiplicity of single acoustic transducers 30 each formed from a small piezoelectric rod 35 respectively are disposed in a regular, e.g. square, grid, with their longitudinal extension aligned perpendicular to the grid plane. These single acoustic transducers 30 are embedded in a polymer matrix 31 for the purpose of reciprocal isolation and for transmitting the generated sound (FIGS. 4a, 4b). Such type composites are fabricated according to the dice and fill process, with first plane-parallel plates 33 being cut into a square block of piezoelectric material down to a base area 34 (FIG. 5b), and then in a next step plates 33 being cut to small rods 35 standing on the base area 34 in transverse direction to the first cutting direction. These small rods are poured together with the base area 34 into the polymer matrix 31 (FIG. 5d). Finally the base area 34 is worked off, for example by polishing, in such a manner that the small rods 35 remain as single acoustic transducers 30 in the polymer matrix 31 and can be connected with respective contact elements for impingement with an electric frequency signal. This electrode can also be structured in the form of single elements (ultrasonic array).

An electric control means for activating the single acoustic transducers 30 is provided with a frequency generator 40, a phase shift means 41 and a phase control means 42. The frequency generator 40 generates an electric frequency signal with a frequency of at least 100 kHz and, in particular from 500 kHz to 5 Mhz. This frequency signal is fed to the phase shift means 41, which is provided with a multiplicity of phase shifters with which the phases of the incoming frequency signals can be changed, with phase shift means 41 being provided with a separate output for each single acoustic transducer 30 in such a manner that a phase signal can be emitted for each single acoustic transducer 30 independent of the other single transducers 30. The single phase shifters are controlled by a phase control means 42.

The predetermined phase differences of the individual single acoustic transducers 30 yield the controllable constructive and destructive interferences of the generated sound waves thereby yielding exact focusing without any additional mechanical focusing means and very precise three-dimensional intensity distribution. Moreover, the focusing can be changed quasi as quickly as desired. Preferably, a thin, small plate-like coupling element 22 made of a soft loss-free polymer or a plastic body filled with a liquid is disposed on the electroacoustic transducer device 7. When using the single acoustic transducers 30 embedded in a polymer matrix 31, the polymer matrix 31 itself can be utilized as the coupling element, that is the individual sample receptacles 13 are placed immediately on the electroacoustic transducer device 7 which is designed as a composite. A liquid can also be employed as the coupling layer.

The electronic activation of the single acoustic transducers 30 disposed in a two-dimensional array permits both sequential and parallel exposure of the individual sample receptacles 30 to sound waves. This array arrangement of the single acoustic transducers 30 also permits further miniaturization of the ultrasonic device with ideal, adjustable-at-will and quickly changeable intensity distributions so that even complicated processes for exposing samples to ultrasonic waves can be conducted simply, quickly and, in particular, automatically.

The piezoelectric composites are especially advantageous for the invented device, because they permit effective, broad band sound generation and coupling, simple further processing and wide-ranging adjustability of the electroacoustic properties. However, such array arrangements can also be fabricated in the conventional manner from piezoceramic elements, for example lead zirconate titanate elements, with the electronics for their activation being essentially the same.

A major advantage of the array arrangement is that a multiplicity of samples in the sample receptacles of a micro-titer plate or in another cartridge system can be selectively exposed to ultrasonic waves sequentially or in parallel or in any other sequence without any relative movement between the sample receptacles and the electroacoustic transducer device. As no relative movement is necessary, the sample receptacles do not have to be moved when a multiplicity of samples are treated, thereby preventing cross contamination and obviating renewed mechanical coupling of the electroacoustic transducer device to the receptacle every time, which has to be done with extreme care in order to obtain the desired, reproducible coupling conditions.

In summary it can be said that the present invention permits exact, reproducible coupling of the sound waves into the receptacles of the sample, thereby making the field intensities generated in the sample receptacles exactly adjustable and dosable. By this means, special chemical, biological or microbiological effects can be selectively activated in the samples. Moreover, selective focusing on extremely small sample volumes permits reducing respectively completely preventing interference effects.

List of Reference Numbers

1 Base plate
2 Rails
4 Tie-bar
5 Double arrow
7 Electroacoustic transducer device
8 Double arrow
10 Lateral wall
12 Micro-titer plate
13 Receptacle of the sample
14 Body
15 Electroacoustic transducer
17 Holding means
19 Acoustic lens
20 Spherical surface
22 Coupling element
24 Floor of the receptacle
30 Single acoustic transducer
31 Polymer matrix
33 Plates
34 Base
35 Small rods
40 Frequency generator
41 Phase shifter means
42 Phase control means

What is claimed is:

1. A device for selective exposure of a biological sample to sound waves, comprising:
    one or more receptacles in which said sample is maintained in a suspended form, said receptacle having a surrounding wall and wherein a plane-parallel acoustic $\lambda/4$ wave transformer is provided in said surrounding wall for sound wave coupling;
    an electroacoustic transducer device which generates said sound waves, the electroacoustic transducer disposed outside said receptacle in such a manner that soundwave coupling into said sample occurs through the wall of said receptacle, said electroacoustic transducer device generating sound waves with a frequency of at least 100 kHz; and
    means for focusing said generated sound waves to a sample volume of approximately 50 $\mu l$ in said receptacle.

2. The device according to claim 1, wherein a non-solid polymer element is joined to said electroacoustic transducer device for providing said sound wave coupling to said receptacle.

3. The device according to claim 1, further comprising a liquid coupling element joinable to said electroacoustic transducer device for providing said sound wave coupling to said receptacle.

4. The device according to claim 3, wherein said liquid coupling element comprises degassed water or another liquid that transmits sound.

5. The device according to claim 1, wherein said electroacoustic transducer device further comprises an electroacoustic transducer made of a piezoelectric, magnetostrictive and/or electrostrictive material.

6. The device according to claim 5, wherein said electroacoustic transducer device further comprises a plurality of transducer elements which are joined to said one or more receptacles for providing sound wave coupling to said receptacles, and a control means for focusing said transducer elements, said control means designed in such a manner that said transducer elements are activated with predetermined phase differences such that predetermined focusing is yielded due to constructive and destructive interferences of the generated sound waves.

7. The device according to claim 6, wherein said transducer elements are arranged evenly distributed in a two-dimensional arrangement.

8. The device according to claim 6, wherein the receptacles are exposed to sound waves serially or in parallel without any relative movement between said samples and said transducer device.

9. The device according to claim 1, wherein said means for focusing are adjustable and configured such that the sound waves are concentrated on said sample at a distance from a mean filling level inside said receptacle.

10. The device according to claim 1, wherein said transducer device comprises a piezocomposite provided with a plurality of piezoelements which are embedded as transducer elements in a polymer matrix.

11. The device according to claim 10, wherein said piezoelements are rod-shaped and are disposed in a regular grid in said matrix.

12. The device according to claim 11, wherein said rod-shaped piezoelements are aligned with their longitudinal axes perpendicular to the grid plane, and wherein said piezoelements are disposed in a matrix-like configuration.

13. The device according to claim 1, wherein said electroacoustic transducer device is disposed on an X-Y sled which is moveable in one plane, thereby allowing automatic treatment of several samples.

14. The device according to claim 1, wherein said receptacle is a part of a micro-titer plate, said micro-titer plate having a plurality of said sample receptacles.

15. The device according to claim 1, wherein said sound coupling from said transducer into said wall of said receptacle occurs via a liquid.

16. The device according to claim 1, wherein said sample is biological cell material.

17. The device according to claim 1, wherein said device permits precise intensity dosage of said sound waves to said biological sample for selective excitation of biological effects.

18. The device according to claim 1, wherein said wall of said receptacle comprises a floor.

19. The device according to claim 18, wherein said electroacoustic transducer device is provided below said floor of said receptacle and wherein said sound wave coupling occurring through said floor of said sample receptacle.

20. The device according to claim 19, wherein said floor of said sample receptacle is comprised of acousticalllly suited materials, selected from the group consisting of polystyrol, polypropylene and polyethylene.

21. The device according to claim 19, wherein said floor of said receptacle is comprised of a membrane-like material.

22. A method for treating biological samples, comprising subjecting a multiplicity of samples to sound waves using the device as recited in claim 1.

23. A device for selective exposure of a biological sample to sound waves, comprising:
- one or more receptacles in which said sample is maintained in a suspended form, said receptacle having a surrounding wall;
- an electroacoustic transducer device which generates said sound waves, the electroacoustic transducer disposed outside said receptacle in such a manner that sound-wave coupling into said sample occurs through the wall of said receptacle said electroacoustic transducer device generating sound waves with a frequency of at least 100 kHz; and
- a spherical acoustic lens inserted in said wall of said receptacle focusing said generated sound waves to a sample volume of approximately 50 µl in said receptacle.

24. The device according to claim 23, wherein a non-solid polymer element is joined to said electroacoustic transducer device for providing said sound wave coupling to said receptacle.

25. The device according to claim 23, further comprising a liquid coupling element joinable to said electroacoustic transducer device for providing said sound wave coupling to said receptacle.

26. The device according to claim 25, wherein said liquid coupling element comprises degassed water or another liquid that transmits sound.

27. The device according to 23, wherein said electroacoustic transducer device further comprises an electroacoustic transducer made of a piezoelectric, magnetostrictive and/or electrostrictive material.

28. The device according to claim 27, wherein said electroacoustic transducer device further comprises a plurality of transducer elements which are joined to said one or more receptacles for providing sound wave coupling to said receptacles, and a control means for focusing said transducer elements, said control means designed in such a manner that said transducer elements are activated with predetermined phase differences such that predetermined focusing is yielded due to constructive and destructive interferences of the generated sound waves.

29. The device according to claim 28, wherein said transducer elements are arranged evenly distributed in a two-dimensional arrangement.

30. The device according to claim 28, wherein the receptacles are exposed to sound waves serially or in parallel without any relative movement between said samples and said transducer device.

31. The device according to claim 23, wherein said spherical acoustic lens is adjustable and configured such that the volume of said sample into which the sound waves are concentrated on said sample at a distance from a mean filling level inside said receptacle.

32. The device according to claim 23, wherein said transducer device comprises a piezocomposite provided with a plurality of piezoelements which are embedded as transducer elements in a polymer matrix.

33. The device according to claim 32, wherein said piezoelements are rod-shaped and are disposed in a regular grid in said matrix.

34. The device according to claim 33, wherein said rod-shaped piezoelements are aligned with their longitudinal axes perpendicular to the grid plane, and wherein said piezoelements are disposed in a matrix-like configuration.

35. The device according to claim 23, wherein said electroacoustic transducer device is disposed on an X-Y sled which is moveable in one plane, thereby allowing automatic treatment of several samples.

36. The device according to claim 23, wherein said receptacle is a part of a micro-titer plate, said micro-titer plate having a plurality of said sample receptacles.

37. The device according to claim 23, wherein said sound coupling from said transducer into said wall of said receptacle occurs via a liquid.

38. The device according to claim 23, wherein said sample is biological cell material.

39. The device according to claim 23, wherein said device permits precise intensity dosage of said sound waves to said biological sample for selective excitation of biological effects.

40. The device according to claim 23, wherein said wall of said receptacle comprises a floor.

41. The device according to claim 40, wherein said electroacoustic transducer device is provided below said floor of said receptacle and wherein said sound wave coupling occurring through said floor of said sample receptacle.

42. The device according to claim 41, wherein said floor of said sample receptacle is comprised of acoustically suited materials, selected from the group consisting of polystyrol, polypropylene and polyethylene.

43. The device according to claim 41, wherein said floor of said receptacle is comprised of a membrane-like material.

44. A method for treating biological samples, comprising subjecting a multiplicity of samples to sound waves using the device as recited in claim 23.

45. A method for treating biological samples with sound waves, the method comprising the steps of:
- (a) placing said biological samples into on or more receptacles in a micro-titer place such that said samples are maintained in suspended form, said receptacles having a surrounding wall wherein a plane parallel acoustic $\lambda/4$ wave transformer is provided in said surrounding wall;
- (b) positioning said receptacles to correspond with a plurality of electroacoustic transducer elements in an electroacoustic transducer device positioned outside said micro-titer plate;
- (c) subjecting said samples in said receptacles to sound waves generated by said electroacoustic device.

46. The method according to claim 45, wherein said samples are subjected to said sound waves via sound-wave coupling into said sample through the wall of said receptacles.

47. The method according to claim 45, wherein said electroacoustic transducer device generates sound waves having a frequency of at least 100 kHz.

48. The method according to claim 45, wherein said subjecting step (d) further comprises the step of focusing said generated sound waves on to said samples in said receptacles via a spherical acoustic lens inserted in said wall of said receptacles.

49. The method according to claim 48, wherein said generated sound waves are focused on a sample volume of approximately 50 µl in each of said receptacles.

50. The method according to claim 45, wherein said positioning step (b) further comprises the step of joining each of said transducer acoustic elements with each of said receptacles for providing sound-wave coupling into said sample through the walls of said receptacle.

51. The method according to claim 50, wherein the sounds waves have frequency of at least 100 kHz.

52. The method according to claim 45, wherein said sample is biological cell material.

53. The method according to claim 45, wherein said device permits precise intensity dosage of said sound waves to said biological sample for selective excitation of biological effects.

54. The device according to claim 45, wherein said wall of said receptacles comprises a floor.

* * * * *